US012714349B2

(12) United States Patent
Sauter-Starace et al.

(10) Patent No.: US 12,714,349 B2
(45) Date of Patent: Aug. 25, 2026

(54) NEURAL ACTIVITY MEASURING SYSTEM WITH IMPROVED FIXING DEVICE

(71) Applicant: Commissariat à l'Energie Atomique et aux Energies Alternatives, Paris (FR)

(72) Inventors: Fabien Sauter-Starace, Grenoble Cedex (FR); Guillaume Charvet, Grenoble Cedex (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 385 days.

(21) Appl. No.: 18/493,852

(22) Filed: Oct. 25, 2023

(65) Prior Publication Data

US 2024/0138739 A1 May 2, 2024

(30) Foreign Application Priority Data

Oct. 26, 2022 (FR) ..................................... 22 11128

(51) Int. Cl.
*A61B 5/291* (2021.01)
*A61B 5/00* (2006.01)
(Continued)

(52) U.S. Cl.
CPC ............ *A61B 5/293* (2021.01); *A61B 5/6868* (2013.01); *A61B 2560/0412* (2013.01)

(58) Field of Classification Search
CPC ......... A61B 5/291; A61B 5/24; A61B 5/4094; A61B 5/369; A61B 5/293; A61B 5/372;
(Continued)

(56) References Cited

U.S. PATENT DOCUMENTS 7,346,391 B1 3/2008 Osorio et al.
7,917,222 B1 3/2011 Osorio et al.
(Continued)

FOREIGN PATENT DOCUMENTS

EP 2 623 025 B1 6/2017

OTHER PUBLICATIONS

French Preliminary Search Report issued Apr. 7, 2023 in French Application 22 11128 filed on Oct. 26, 2022, 9 pages (with English Translation of Categories of Cited Documents & Written Opinion).

*Primary Examiner* — Joseph A Stoklosa
*Assistant Examiner* — Brian M Antiskay
(74) *Attorney, Agent, or Firm* — Oblon, McClelland, Maier & Neustadt, L.L.P.

(57) ABSTRACT

A system for measuring the neural activity of a living being, including an implantable measuring device equipped with a housing to be accommodated, at least partially, in a cavity formed in the cranium (C) of a living being, and including a system of electrodes for measuring the neural activity, arranged on one face of the housing, and electronic signal-processing device, which are accommodated in the housing and to which the electrode system is connected, a device for fixing the housing in the cavity, the fixing device including at least one device for mechanically holding the housing in the cavity, a device for fixing the mechanical holding device, which are arranged to fix the holding device in the cranium (C) on the periphery of the cavity, a device for adjusting the depth position of the housing in the cavity.

5 Claims, 3 Drawing Sheets

(51) Int. Cl.

| | |
|---|---|
| ***A61B 5/24*** | (2021.01) |
| ***A61B 5/293*** | (2021.01) |
| ***A61B 5/369*** | (2021.01) |

(58) Field of Classification Search

CPC . A61B 18/1492; A61B 5/0031; A61B 5/6868; A61B 5/0006; A61B 5/6803; A61B 5/37; A61B 5/6814; A61B 5/388; A61B 5/6864; A61B 2018/00839; A61B 5/4064; A61B 5/282; A61B 5/25; A61B 5/165; A61B 2018/1475; A61B 18/082; A61N 1/0529; A61N 1/0531; A61N 1/0539; A61N 1/0534; A61N 1/37514; A61N 1/3605; A61N 1/0558; A61N 1/3756; A61N 1/37518; A61N 1/0472

USPC .................................. 600/372–393, 544–545

See application file for complete search history.

(56) References Cited

U.S. PATENT DOCUMENTS

| | | | | |
|---|---|---|---|---|
| 8,454,701 | B2 * | 6/2013 | Devauchelle | A61N 1/375 623/17.19 |
| 8,862,235 | B1 * | 10/2014 | Stover | A61B 5/293 607/45 |
| 2004/0034368 | A1 * | 2/2004 | Pless | A61N 1/37518 606/129 |
| 2007/0156126 | A1 * | 7/2007 | Flaherty | A61B 5/6885 606/32 |
| 2007/0233158 | A1 * | 10/2007 | Rodriguez | A61N 1/0539 606/130 |
| 2009/0112327 | A1 * | 4/2009 | Lane | A61B 90/10 623/16.11 |
| 2013/0204317 | A1 | 8/2013 | Sauter-Starace et al. | |
| 2017/0007828 | A1 * | 1/2017 | Monteiro | A61N 1/0534 |
| 2018/0085573 | A1 * | 3/2018 | Alam | A61N 1/0539 |
| 2018/0256888 | A1 * | 9/2018 | Wingeier | A61N 1/0492 |

* cited by examiner

NEURAL ACTIVITY MEASURING SYSTEM WITH IMPROVED FIXING DEVICE

TECHNICAL FIELD OF THE INVENTION

The present invention relates to a system for measuring the neural activity of a living being, the system being equipped with an improved fixing device.

PRIOR ART

There are many devices implantable in the brain of a living being, used for reading, recording and/or monitoring neural signals.

The patent documents EP2623025B1, WO2011/123150A1, WO2011/067297A1 and U.S. Pat. No. 7,747,318B2 describe various devices for measuring the neural activity of a living being.

These devices generally comprise a housing which is accommodated partially or completely in a cavity (after a craniotomy) made on the skull. It also comprises a system of electrodes for measuring neural activity, arranged on one face of the housing, and electronic signal-processing means accommodated in the housing. It also comprises at least one antenna coupled to the electronic means in order to send measured data to a remote terminal.

In some cases, the device can be perfectly integrated and follow the shape of the skull (as in the patent EP2623025B1), or it can comprise a part housed in the skull and a part protruding with respect to the surface of the skull (as in the patent application WO2011/123150A1).

This type of measuring device must satisfy several conditions:

- it must be perfectly positioned and not move in its cavity, whatever the activity of the patient;
- it must also be positioned so that its electrode system comes as closely as possible into contact with the brain in order to optimize the measurement;
- it must make it possible to avoid any injury, notably in the event of an impact;
- it must be able to be easily located, even after wound healing.

The object of the invention is to propose a measuring system making it possible to satisfy one or more of the conditions mentioned above.

SUMMARY OF THE INVENTION

This object is achieved by a system for measuring the neural activity of a living being, comprising:

- an implantable measuring device equipped with a housing to be accommodated, at least partially, in a cavity formed in the cranium of a living being, and comprising a system of electrodes for measuring the neural activity, arranged on one face of the housing, and electronic signal-processing means, which are accommodated in the housing and to which the electrode system is connected,
- a device for fixing the housing in said cavity, the fixing device comprising:
- at least one device for mechanically holding the housing in the cavity,
- means for fixing said mechanical holding device, which are arranged to fix the holding device in the cranium on the periphery of the cavity,
- means for adjusting the depth position of the housing in the cavity,
- means for locating said housing, said locating means comprising one or more permanent magnets.

According to a first embodiment, the mechanical holding device comprises at least one clamping member intended to be screwed into the cranium by said fixing means and arranged to bear against a wing of the housing.

According to one feature, the adjustment means comprise a washer intended to be placed between the wing of the housing and a bearing surface situated on the periphery of the cavity, the thickness of the washer defining the depth of engagement of the housing in the cavity.

According to another feature, the clamping member comprises one or more receptacles, each intended to receive, in a removable manner, at least one permanent magnet.

According to another feature, the clamping member is made of a non-magnetic and electrically non-conductive material.

According to a second embodiment, the mechanical holding device comprises a receiving part intended to be accommodated in the cavity, fixed on the periphery of the cavity by said fixing means, said receiving part carrying said adjustment means.

According to one feature, the adjustment means comprise an internal thread formed on a surface of the receiving part and configured to cooperate with an external thread formed on a surface of the housing.

According to another feature, the system comprises means for locking the housing in depth in the receiving part.

According to another feature, the receiving part comprises one or more receptacles, each intended to receive, in a removable manner, at least one permanent magnet.

According to another feature, the housing and/or the receiving part comprise(s) mechanical means for assisting the screwing of the housing into the receiving part.

According to another feature, the receiving part is made of a non-magnetic and electrically non-conductive material.

According to a third embodiment, the mechanical holding device comprises several clamping members distributed around the housing of the measuring device, each clamping member comprising a body intended to be fixed in the cranium, and a plate adjustable in height with respect to the body and enclosing the housing by its thickness.

According to one feature, the height adjustment means comprise an endless screw cooperating with said plate and with the body of the clamping member.

BRIEF DESCRIPTION OF THE FIGURES

Other features and advantages will become apparent from the following detailed description, which is given with reference to the appended drawings, in which.

DETAILED DESCRIPTION OF AT LEAST ONE EMBODIMENT

Figure 1A:
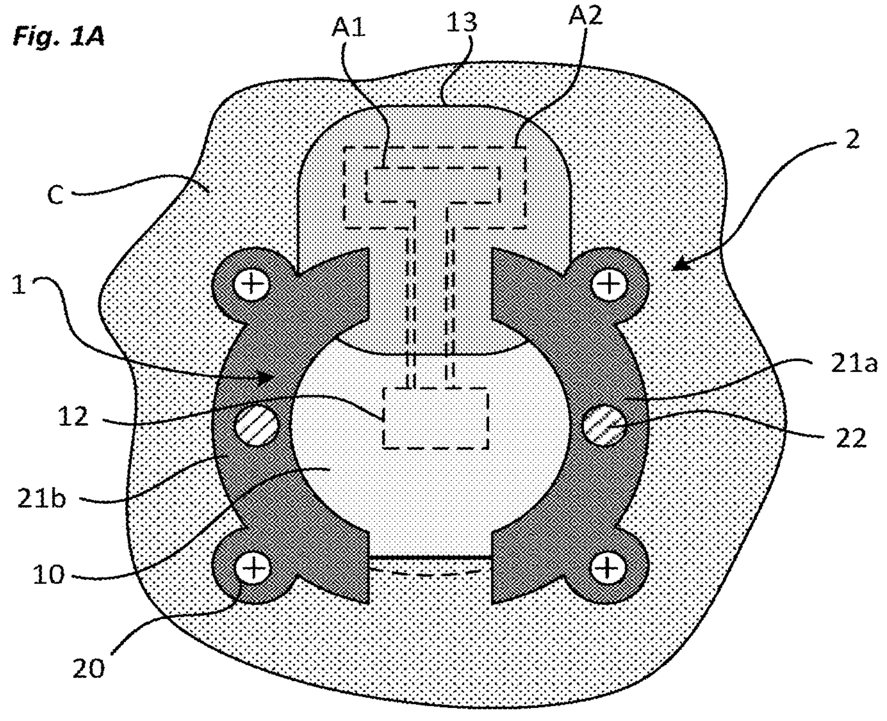
FIGS. 1A and 1B show a first embodiment of the system, respectively in a plan view and in a cross-sectional view.

According to the invention, the measuring system comprises:

- an implantable measuring device 1 equipped with a housing 10 to be accommodated, at least partially, in a cavity (after a craniotomy) formed on the cranium C of a living being, a device 2, 3, 4 for fixing the housing 10 in said cavity.

The measuring device 1 comprises a system 11 of electrodes for measuring the neural activity, arranged on a lower face of the housing 10, said lower face being intended to be oriented towards the bottom of said cavity when the housing is in place. The electrodes 110 are each intended to come into contact with the tissues 5 whose electrical activity is to be measured.

It also comprises electronic signal-processing means 12 (in particular for filtering, amplifying, digitizing the signals), which are accommodated in the housing 10 and to which the electrode system 11 is connected. It can also comprise a data transmission antenna A1 connected to the electronic processing means in order to transfer the digitized data to a remote external terminal, and a remote-feed antenna A2 used to supply energy to the electronic part and/or to charge a battery of the measuring device 1 by inductive coupling. The battery can be accommodated in the housing of the measuring device.

The two antennas A1, A2 can be realized on a support 13 fixed to said housing or they can be integrated around or in the housing. In particular, the remote-feed antenna A1 can be placed in the circumference of the housing a fortiori if the latter is made of titanium (which is a material that penalizes the powering by inductive coupling, in particular at 13.56 MHz). The antenna A2 can be envisaged at the periphery in a ring of the housing, arranged on its upper face or in the housing 10, depending on the telecommunication frequencies and on the expected performance.

According to the invention, the fixing device 2, 3, 4 of the system is arranged to hold the housing 10 in the cavity made in the cranium C and to allow the electrodes 110 to be held in abutment against the tissues 5.

The fixing device 2, 3, 4 comprises at least one mechanical holding device, responsible for holding the housing 10 in its cavity.

The fixing device 2, 3, 4 also comprises fixing means arranged to fix the mechanical holding device in the cranium C, on the periphery of the cavity, in order to hold the housing 10 in the cavity.

These fixing means can advantageously comprise several screws 20, 30, 40 of the self-drilling type passing through the holding device at several points and intended to be screwed into the cranium C.

According to the invention, the fixing device also comprises means for adjusting the depth position of the housing 10 in the cavity. These adjustment means are intended to position the housing 10 optimally so that its electrode system 11 comes into mechanical contact with the tissues 5, for reliable measurement, without exerting too great a stress.

Figure 1B:
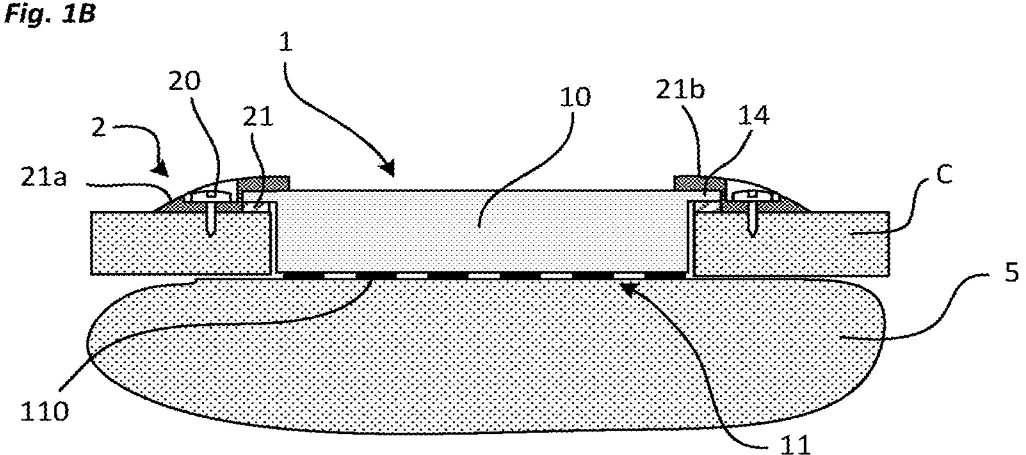

In a first embodiment illustrated by FIG. 1A and FIG. 1B, the mechanical holding device of the fixing device 2 comprises one or more clamping members 21. In this first embodiment, two clamping members 21*a*, 21*b* are used, for example. The two clamping members 21*a*, 21*b* are each made in the form of a half-moon piece which is screwed into the cranium C and bears on one or more lateral wings 14 of the housing 10 of the measuring device. The lateral wings 14 can be replaced by a collar formed all around the housing 10. The wings 14 or the collar are arranged so as to be positioned facing the surface of the cranium C, this surface being present on the periphery of the cavity.

The means for adjusting the depth position of the housing 10 advantageously comprise a washer 21 or equivalent, positioned at the interface between the wings 14 (or the collar) of the housing 10 and the surface of the cranium C situated on the periphery of the cavity. The thickness of the washer 21 makes it possible to adjust the depth position of the housing 10 in the cavity. The washer 21 can be replaced by any other equivalent solution, for example a seal made of flexible material such as implantable silicone or polycarbonate, or rigid material such as, but not limited to, Teflon (registered trademark), PEEK, PEKK or dental cement, etc. Of course, the depth of screwing of the clamping members 21*a*, 21*b* will be adapted according to the thickness of the washer 21. The material used for this adjustment "layer" will of course be chosen to be biocompatible.

Advantageously, each clamping member 21*a*, 21*b* can have a receptacle in which a permanent magnet 22 is placed so as to be removable. The permanent magnets 22 make it possible to better locate the device once it has been implanted, in particular its remote-feed antenna A2, for powering the device or recharging its battery. By virtue of the permanent magnets, it is possible to locate it in position (along X and Y) but also in depth, taking into consideration the intensity of the magnetic field generated. In addition, the use of three permanent magnets (arranged in a triangle) makes it possible to locate the housing with precision (by triangulation).

In a non-limiting manner, the holding device formed by each clamping member can be made of titanium. Alternatively, for MRI compatibility, it can also be made of a biocompatible and insulating polymer such as PEEK or PEKK.

Figure 2A:
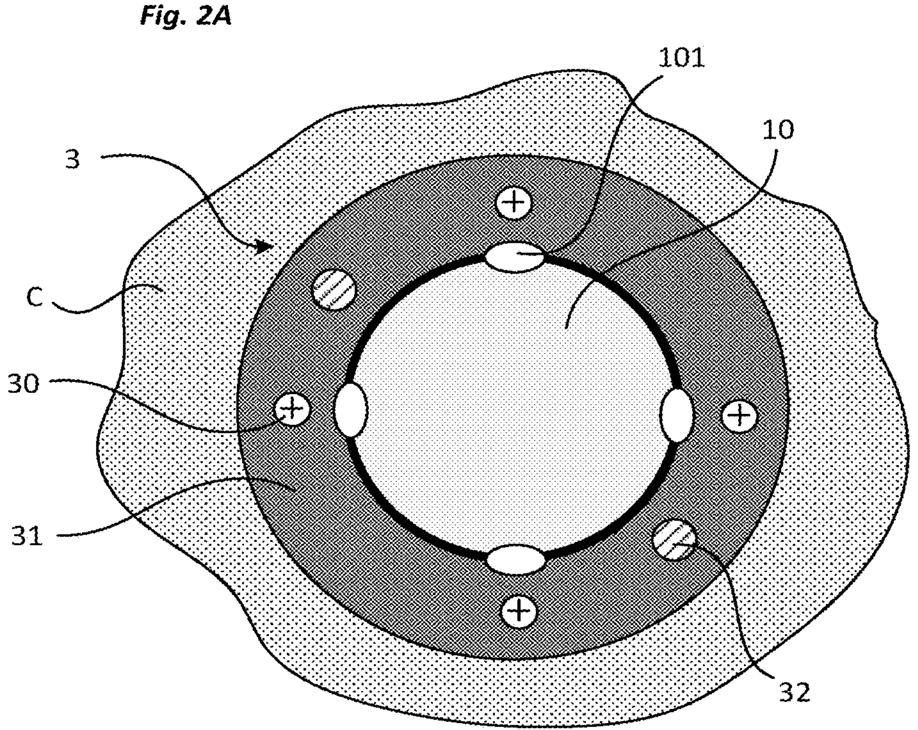
FIGS. 2A and 2B show a second embodiment of the system, respectively in a plan view and in a cross-sectional view.
Figure 2B:
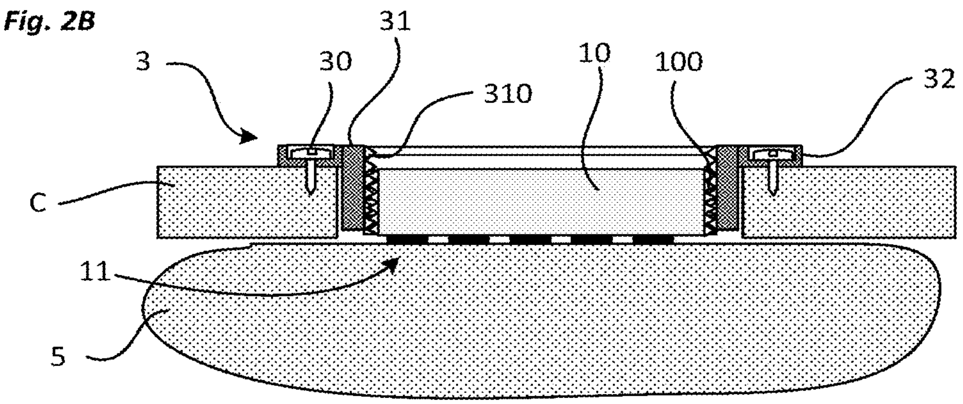

In a second embodiment shown in FIG. 2A and in FIG. 2B, the mechanical holding device of the fixing device 3 comprises a receiving part 31 which is accommodated in the cavity. This receiving part 31 comprises lateral wings 32 or a collar bearing against the surface of the cranium C (outer table) situated on the periphery of the cavity or on a countersink. The fixing means are also formed by self-drilling screws 30 passing through said wings 32 or the collar and penetrating into the cranium C in order to fix the receiving part 31. The screws are distributed on the periphery of the receiving part 31 in order to obtain stable and uniform fixing of the receiving part 31.

The receiving part 31 is made in the form of a tubular part open at the top and at the bottom. It has a cylindrical internal cross section. On its internal lateral face, the receiving part has a thread 310 intended to cooperate with a thread 100 formed on a lateral face of the housing 10 of the measuring device. Screwing the housing 10 into the receiving part 31 makes it possible to adjust the depth position of the measuring device 1 and thus the level of support of its electrode system 11, situated on its lower face, against the tissues 5. The thread angle is preferably adapted to the coefficient of friction of the materials in wet conditions in order to obtain an irreversible thread.

In this embodiment, to ensure the angular hold of the implant during the screwing of the receiving part 31 or the screwing of the housing 10 while the receiving part 31 is wedged in the craniotomy and fixed angularly by means of the self-drilling screws, various means can be envisaged:

Notches 101 can be made in the circumference of the housing 10 at the level of the thread (FIG. 2A—the latter possibly comprising discontinuities). These notches are preferably peripheral and continuous in order to make it easy to assess the cleaning of the implant and to avoid surgical complications related to friction on rough surfaces or edges in the event of contact with the skin;

A tab can be affixed with a biocompatible silicone adhesive offering low adhesion (without adhesion promoter);

A suction cup can be temporarily applied to the upper face of the housing 10 in order to hold the latter or actuate it in rotation with respect to the receiving part.

Locking means can be provided in order to lock the depth position of the housing 10 screwed into the receiving part 31. These locking means may be provided in various ways, for example via a notch and a locking bar, or by means of a non-return clip which is positioned in the thread in order to impede movement of the housing.

The receiving part 31 is made of a biocompatible material that is easy to machine, non-magnetic and insulating, such as PEEK or PEKK. The thread 100 formed on the housing 10 of the measuring device can be obtained by moulding or attached by gluing. The recommended material is also biocompatible and non-magnetic. Similarly, the receiving part 31 can comprise one or more receptacles, each intended to receive a permanent magnet 32 making it possible to locate the housing 10 and its remote-feed antenna A2.

Figure 3A:
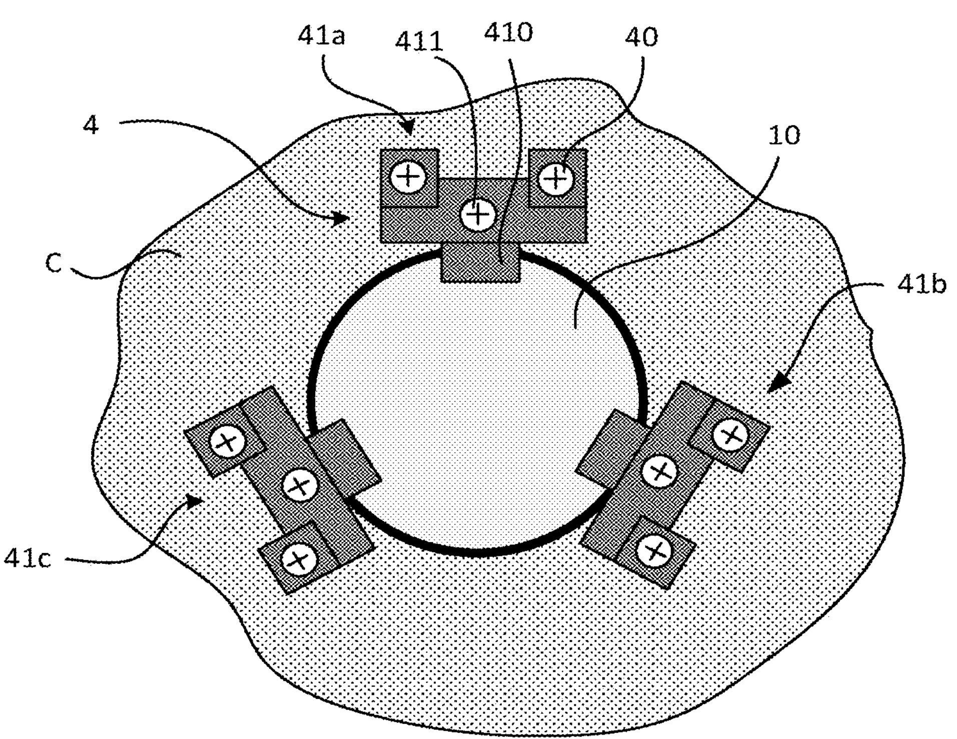
FIGS. 3A and 3B show a third embodiment of the system, respectively in a plan view and in a partial cross-sectional view.
Figure 3B:
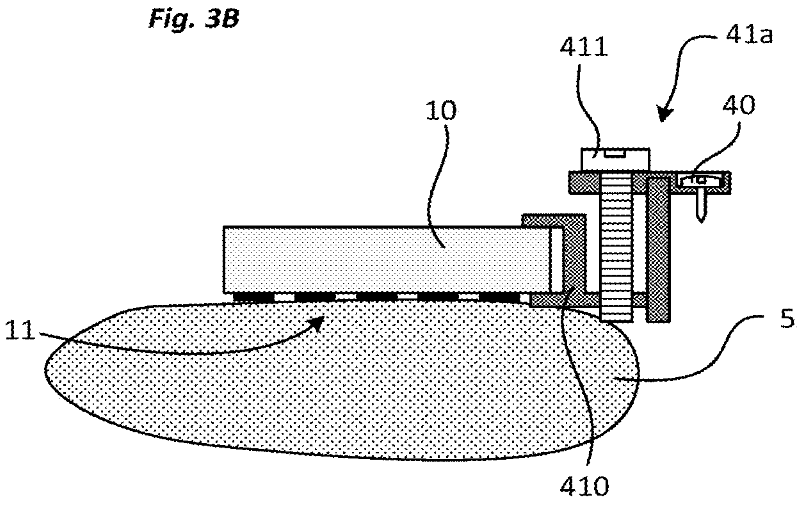

In a third embodiment illustrated by FIG. 3A and FIG. 3B, the mechanical holding device of the fixing device 4 comprises at least three clamping members 41*a*, 41*b*, 41*c*, advantageously identical, separated from one another and distributed around the housing 10 of the measuring device 1. The three clamping members 41 are therefore advantageously disposed at 120° to one another.

Advantageously, each clamping member 41*a*, 41*b*, 41*c* can be fixed in the cranium C via one or more screws 40 (for example of the self-drilling type). Each clamping member 41*a*, 41*b*, 41*c* also comprises a plate 410 adjustable in height and configured to cooperate with the housing 10 of the device. This plate 410 can have a U-shaped cross section, enabling it to grip the housing 10 over its thickness. The height adjustment of the plate 410 can be achieved by means of an endless screw 411 inserted in the body of the clamping member. This adjustment solution makes it possible to obtain fine adjustment of the position of the measuring device 1 (along three axes) and to orient the housing so as to be able to take better account of the shape of the tissues 5 with which the electrode system 11 is brought into contact. Advantageously, the interface with the housing will rather be of the punctiform type in order not to constrain the orientation of the surfaces. The orientation of the plane of the electrode system 11 is adjusted by means of the three endless screws 411, like a tripod.

This version with three clamping members is advantageous in that each of the members can carry a separate permanent magnet, making it easier to locate the housing 10 and its remote-feed antenna A2, by triangulation.

The solution of the invention affords numerous advantages, among which:

it permits a reliable hold of the measuring device in its cavity;

it permits a depth adjustment of the position of the housing of the measuring device, guaranteeing the contact of the electrode system against the tissues, without risk of injury;

it is adapted to the existing measuring device, such as that described in the patent EP2623025B1.

The invention claimed is:

1. A system for measuring the neural activity of a living being, comprising:

an implantable measuring device equipped with a housing to be accommodated, at least partially, in a cavity formed in a cranium (C) of a living being, and comprising a system of electrodes for measuring the neural activity, arranged on one face of the housing, and electronic signal-processing devices, which are accommodated in the housing and to which the electrode system is connected, and a fixing device for fixing the housing in said cavity, wherein the fixing device comprises:

a mechanical holding device for mechanically holding said housing in the cavity, a device for fixing said mechanical holding device, which is arranged to fix the holding device in the cranium (C) on a periphery of the cavity, an adjustment device for adjusting a depth position of the housing in the cavity, and a locating device for locating said housing, said locating device comprising one or more permanent magnets, wherein said mechanical holding device includes at least three clamping members, and wherein each clamping member comprises one or more receptacles, each intended to receive, in a removable manner, at least one permanent magnet of said locating device.

2. The measuring system according to claim 1, wherein each clamping member is made of a non-magnetic and electrically non-conductive material.

3. The measuring system according to claim 1, wherein the at least three clamping members are distributed around the housing of the measuring device, each clamping member comprising a body intended to be fixed in the cranium, and a plate adjustable in height with respect to the body and enclosing the housing by its thickness.

4. The measuring system according to claim 3, wherein the adjustment device comprises an endless screw cooperating with said plate and with the body of the clamping member.

5. The measuring system according to claim 3, wherein the plate presents a U-shaped cross section.

* * * * *